United States Patent [19]

Loveless et al.

[11] 4,193,400
[45] Mar. 18, 1980

[54] INTRAVENOUS NEEDLE ASSEMBLY WITH AIR BLEED PLUG

[75] Inventors: James C. Loveless; Darrel R. Palmer, both of Sandy, Utah

[73] Assignee: The Deseret Company, Sandy, Utah

[21] Appl. No.: 916,657

[22] Filed: Jun. 16, 1978

[51] Int. Cl.² ............................................. A61M 5/00
[52] U.S. Cl. ..................... 128/214.4; 128/DIG. 16; 128/221; 138/40
[58] Field of Search ........ 128/214 R, 214.4, DIG. 16, 128/274, 348, 221; 137/197, 199, 513.5, 517, 848, 849; 138/40, 44; 73/425.4 P

[56] References Cited

U.S. PATENT DOCUMENTS

| | | | |
|---|---|---|---|
| 223,396 | 1/1880 | Shabley | 137/848 |
| 425,530 | 4/1890 | Wayte | 137/848 |
| 2,969,066 | 1/1961 | Holter et al. | 128/350 V |
| 3,055,361 | 9/1962 | Ballard | 128/214.4 |
| 3,859,998 | 1/1975 | Thomas et al. | 128/214.4 |

*Primary Examiner*—Dalton L. Truluck
*Attorney, Agent, or Firm*—Lynn G. Foster

[57] ABSTRACT

An intravenous needle assembly and an associated manufacturing method, wherein the needle assembly comprises a hypodermic needle attached to a hub at its trailing end, a transparent blood detection chamber integral with the hub, a catheter disposed around the needle and the needle hub and a plug closing the blood detection chamber, the plug having air breathing means so that upon venipuncture blood from a vein may flow through the needle into the blood detection chamber without substantial air resistance to such flow to visually confirm the accuracy of the introduction of the needle into a vein. The plug is centrally hollow and has an axially directed leading breather projection connected to an annular shoulder or flange. The breather projection comprises a symmetrical hollow truncated conical extension with a hollow interior and walls having a plurality of narrow slits permitting ready passage of air under pressure of the heart while substantially preventing the passage of blood through the slits. The slits are preferably formed during molding of the plug, using molds wherein the apexes of a male mold are made to line contact the inner conical surface of a female mold to form each slit during injection molding of the plug.

10 Claims, 5 Drawing Figures

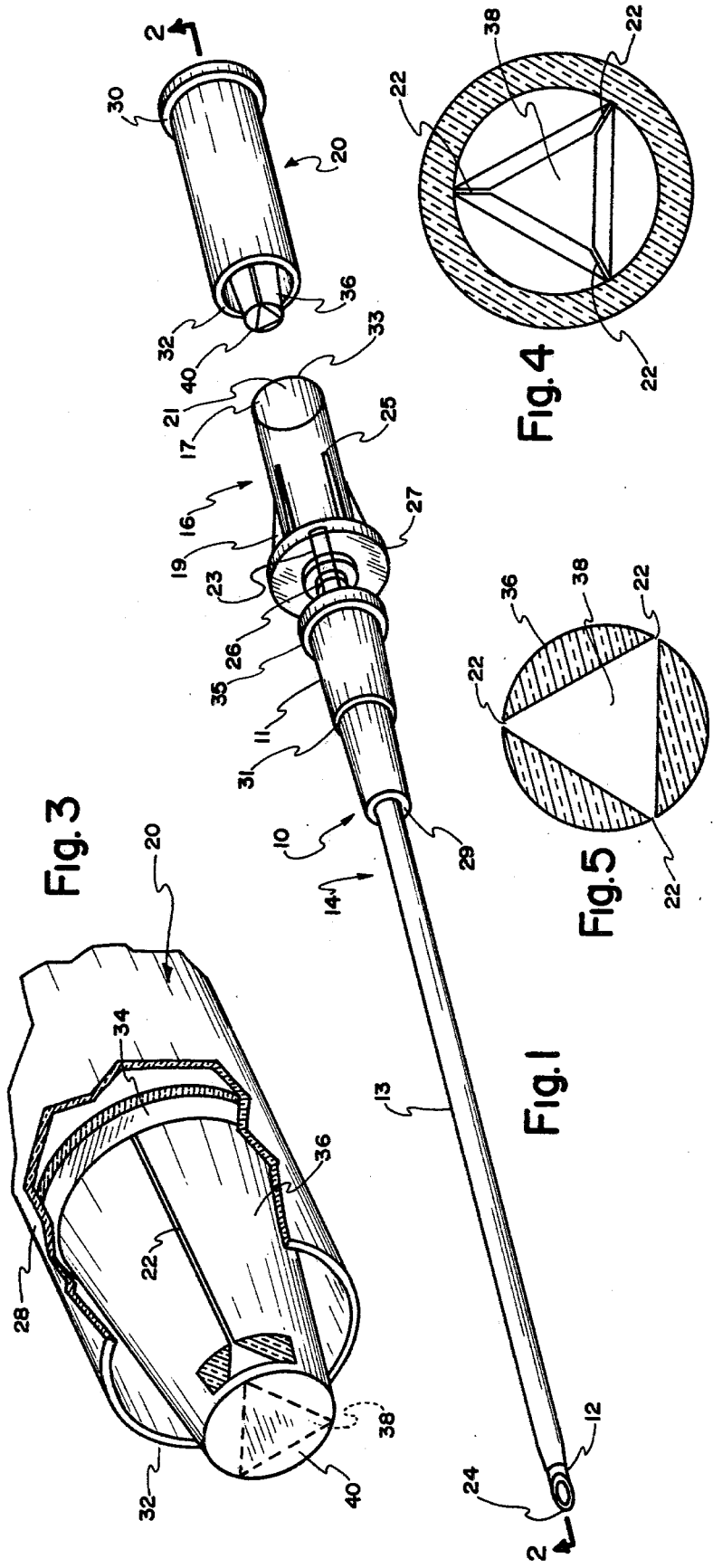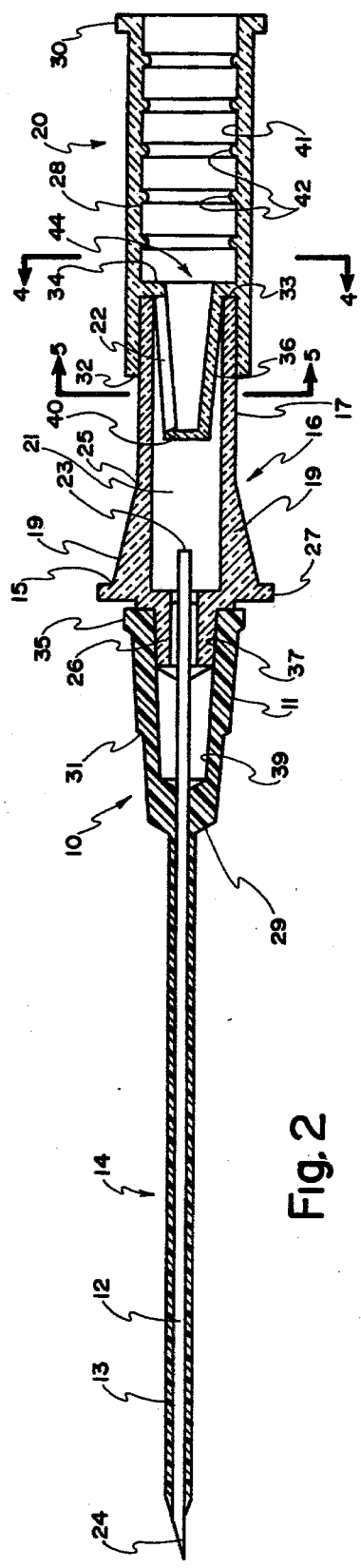

INTRAVENOUS NEEDLE ASSEMBLY WITH AIR BLEED PLUG

BACKGROUND

1. Field of Invention

The present invention relates broadly to intravenous needle assemblies (catheter placement assemblies) and more particularly to needle assemblies comprising a hypodermic needle with a pointed end and a hub secured along the blunt end thereof, the hub carrying a transparent blood detection or flashback chamber so that the proper introduction of the needle into the vein can be ascertained by a showing of blood from said needle, within the blood detection chamber, while simultaneously permitting entering blood and displacement of air, but not blood from the interior of the detection chamber.

2. Prior Art

Heretofore, intravenous needle assemblies have employed metal needles and hubs, sometimes permitting no visual observation of blood following venipuncture until blood flows from the trailing end thereof. In other instances, transparent flashback chambers have been provided integral with a hub to permit early detection of the blood after it passes beyond the needle of the intravenous needle assembly. Still other such assemblies have employed plugs with an air removal feature. Some of these are not effective to reliably evacuate air; some require a separate operation to provide a uniform slit in a radial diaphragm. See U.S. Pat. No. 3,859,998. Such slits are expensive to produce and the end product is not of consistent reliability. Consequently, it has been a long standing problem to dependably produce air breather caps which are economical and effective to exhaust air while obviating blood loss following venipuncture. Additionally, the methods of producing breather caps or plugs are expensive and have sometimes created safety problems, e.g. the danger of loose particles. Further, prior art air bleed plugs contain a single narrow opening which may in any particular use be so oriented or clogged as to not permit full evacuation of air from the interior of the intravenous needle assembly.

BRIEF SUMMARY AND OBJECTS OF THE INVENTION

The present invention comprises an intravenous needle (catheter placement) assembly and an associated manufacturing method, the assembly comprising a hypodermic needle with an attached hub and flashback chamber which chamber is light transmitting so that blood therein may be visually verified, a pliant catheter tube disposed around the needle and the needle hub, and a novel breather plug substantially closing the flashback chamber but accommodating evacuation of air therefrom while preventing leakage of blood into the plug. The plug is uniquely configured with one or more side wall openings to permit said air evacuation without blood loss.

With the foregoing in mind it is a primary object of this invention to provide a novel and improved intravenous needle or catheter placement assembly.

It is another paramount object of the invention to provide an intravenous needle assembly with a novel breather plug to prevent the flow of blood from the assembly while permitting the exhausting of air from the assembly following venipuncture.

It is another important object of the invention to provide an intravenous needle assembly which may be accurately introduced into the vein for subsequent use in infusing fluid into the vein, while preventing the introduction of foreign particles into the vein.

It is another significant object of this invention to provide a novel air evacuation plug for an intravenous needle assembly having at least one elongated narrow side wall passage permitting the discharge of air from the assembly.

It is another paramount object of the invention to provide an intravenous needle assembly having an air evacuation plug providing for substantially complete evacuation of the air therein.

It is another object of this invention to provide an air exhaust plug having at least one elongated side wall passage for air displacement therethrough but preventing flow of blood at said passage, the passages formed automatically during the manufacture of the plug without subsequent operations.

It is a still further valuable object of this invention to provide an air bleed plug for an intravenous needle assembly having narrow side wall openings fabricated therein without the removal of material in the formation thereof.

It is a still further primary object of this invention to provide an improved air bleed plug and a manufacturing method of creating said air bleed plug for an intravenous needle assembly.

These and other objects and features of the present invention will be apparent from the detailed description taken with reference to the accompanying drawings.

BRIEF DESCRIPTION OF THE DRAWINGS

FIG. 1 is a perspective of a partially exploded view of an intravenous needle or catheter placement assembly according to the present invention showing the air breather plug in a position removed from the end of the blood detection chamber;

FIG. 2 is a longitudinal cross-sectional view of the needle assembly taken along the line 2—2 of FIG. 1, showing the air breather plug disposed within the trailing end of the blood detection chamber;

FIG. 3 is an enlarged perspective view of the air breather plug or cap with parts broken away for clarity;

FIG. 4 is a cross-sectional view of the plug taken along line 4—4 of FIG. 2; and FIG. 5 is a cross-sectional view of the plug taken along line 5—5 of FIG. 2.

DETAILED DESCRIPTION OF THE ILLUSTRATED EMBODIMENT

Reference is now made specifically to the drawings, wherein like numerals are used to designate like parts throughout. Referring to FIGS. 1 and 2, the preferred embodiment of the intravenous needle (catheter placement) assembly of the present invention is shown and is generally designated 10. The intravenous needle assembly 10 comprises a hollow hypodermic needle 12 which has a sharp bevelled point 24 on the leading end thereof. The trailing end 23 of the needle 12 is suitably secured in fluid tight relation within a hollow cylindrical plastic needle hub 26. The hub 26 merges into an exposed radial flange 27. The trailing blunt end 23 extends a short distance within the hollow interior 21 of blood detection chamber 16. Blood detection chamber 16 comprises an elongated axially hollow cylinder 17 which is unitarily joined to radial flange 27 at the forward end of cylinder 17 adjacent to said needle hub 26. A plurality of projecting strengthening ribs 19 are evenly spaced around the circumference of cylinder 17. The ridges 19 at their greatest height 15 are contiguous with the rear-side edge of the radial flange 27 and each tapers gradually into cylinder 17 at point 25. The ridges 19 and flange 27 facilitate easy manual manipulation of said assembly. The needle hub 26 and the blood detection chamber 16 are preferably molded together as one integral part and are preferably made of light transmitting plastic. The trailing end 33 of the cylinder 17 comprises a narrow edge circumscribing an opening.

A catheter tube assembly 14 is superimposed over the needle 12 and comprises a flexible hollow plastic catheter tube 13 which is suitably attached to a hollow rigid plastic hub 11. The hub 11 comprises an interior hollow chamber 39. The hub 11 also comprises an exposed shoulder 29 at the trailing end of said catheter tube 13. The exterior of hub 11 is essentially a truncated cone having a small central step 31. The exterior of the hub 11 at the proximal end comprises luer lugs 35 by which a syringe or intravenous set may be attached to the hub 11 for fluid infusion following venipuncture and needle removal. The needle hub 26 is frictionally retained within the hollow interior of the hub 11 in fluid tight relation along interface 37 in the assembled condition. (See FIG. 2.)

An air bleed plug 20, adapted to be force-fit over the trailing end of the detection chamber 16, is shown removed from blood detection chamber 16 in FIG. 1. In FIG. 2 the air bleed plug 20 is shown in its installed or assembled position snugly around the trailing end of air detection chamber 16 forming an air tight seal therewith. The air bleed plug 20 in its presently preferred embodiment comprises an elongated axially hollow plastic cylindrical body 28. At the trailing end of the body 28 is a projecting exterior annular flange 30 to facilitate manual gripping and handling.

The interior 41 of the cylindrical body 28 of air bleed plug 20 may be axially lined with one or more small strengthening radial ribs 42. The plug 20 comprises a forward edge 32 to the hollow cylindrical body 28. A membrane 44 spans across and substantially closes the interior of the cylindrical body 28 a small distance to the rear of edge 32. The membrane 44 comprises an annular shoulder 34, which unitarily connects to the body 28, and a forwardly directed male bleeder projection 36. The projection is integral with annular shoulder 34 and extends forward a distance beyond the edge 32 of the cylinder 28. In configuration the projection 36 is illustrated as being a truncated cone but may be any other suitable shape. Truncated cone 36, while having an exterior cone shape, has a hollow interior in the form of an equilateral triangular cavity 38 when viewed in cross-section. (See FIG. 4.) The cavity is tapered at the same angle of inclination as the exterior truncated cone 36. The triangular cavity 38 is sealed at blunt end 40. It is apparent by observation of the Figures that the three corners or apexes of the triangular cavity 38 slightly intersect the exterior surface of the truncated conical projection 36. (See especially FIG. 5.) Hence, very narrow slits 22 are created and extend substantially the entire length of truncated cone projection 36 from shoulder 34 to blunt end 40. The narrow slits are sized to allow air to escape from the interior of the needle 12 and the interior of the blood detection chamber 16 under pressure of the cardiovascular system of a patient following venipuncture. This provides room for the inflow of blood into the interior of the blood detection chamber 16 through needle 12 and rapidly accommodates visual confirmation of the accurate insertion of the needle 12 into a vein.

The narrow slits 22 not only allow passage of air therethrough to the atmosphere, but substantially prevent loss of blood which has ingressed into detection chamber 16 due to surface friction and the viscosity of the blood. The slits 22 are preferably formed during injection molding of air bleed plug 20.

In use, the catheter placement assembly 10 is grasped manually in the vicinity of the blood detection chamber 16. The sharpened tip 24 is caused to penetrate the skin, subcutaneous tissue and vein of a patient such that the needle 12 with superimposed catheter tube is disposed within said vein. The pressure of the cardiovascular system of the patient will cause blood to travel up the hollow cavity of the needle 12 and into the blood detection chamber 16, attached to the trailing end of the needle. Under pressure of said cardiovascular system, air contained within the hollow interior of the blood detection chamber 16 is caused to pass through the slits 22 in the projection 36 of the plug 20 and into the atmosphere.

Once blood is visibly confirmed by the user as being present in light transmitting chamber 16, the needle 12 together with blood detection chamber 16 and plug 20 are removed from the catheter tube assembly and discarded. The catheter tube assembly 14 is either plugged for subsequent use or connected to a syringe or intravenous set for fluid infusion through the catheter tube 13 into the vein.

Blood present in detection chamber 16 prior to removal of the needle is restrained in the chamber 16 by the nature and sizing of the slits 22 in the sidewall of the projection 36 by reason of the viscosity of the blood and surface friction. Thus, no blood loss from the catheter placement assembly is sustained during venipuncture and confirmation thereof by observation of blood flow into the detection chamber 16.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. A catheter placement assembly comprising:
   a needle for penetrating the vein of a patient;
   a catheter tube to be placed in the vein and left indwelling after venipuncture;
   a flashback chamber connected to the trailing end of the needle, said flashback chamber having an opening at its trailing end;
   an air bleeder plug formed of a substantially shape-retaining biologically inert material removably secured to the trailing end of the flashback chamber, the plug comprising means substantially closing the trailing end opening of the flashback chamber, said closing means comprising sidewall means in close at least partial contiguous relation with the trailing end of the flashback chamber and continuously open narrow elongated slit means disposed in said sidewall means in continuous gaseous communication across and interposed between the flashback chamber and the atmosphere directly adjacent and closely spaced from the flashback chamber, the elongation of the narrow slit means embodying a substantial longitudinal dimension accommodating egress passage of air to the atmosphere without deflection of the slit means while substantially preventing passage of egress blood through the slit means.

2. A catheter placement assembly according to claim 1 wherein said closing means comprises a forward projection extending into the flashback chamber.

3. A catheter placement assembly according to claim 1 wherein said sidewall means projects into the flashback chamber and said continuously open narrow slit means comprises a plurality of continuously open elongated generally axially directed narrow slits.

4. A cathether placement assembly according to claim 1 wherein said plug comprises a hollow cylindrical shell and said closing means comprises a partition spanning across the hollow interior of the shell, said partition comprising an axial interiorly hollow projection having a closed blunt leading end and a truncated conical sidewall in which a plurality of continuously open slits are longitudinally disposed, said partition further comprising an annular ring integrally interposed between the trailing portion of the projection and the shell.

5. A catheter placement assembly according to claim 4 wherein said hollow cylindrical shell comprises means by which the plug is press-fit to the flashback chamber to substantially close the trailing end opening thereof.

6. A catheter placement assembly comprising:
a needle for penetrating the vein of a patient;
a catheter tube to be placed in the vein and left indwelling after venipuncture;
a flashback chamber connected to the trailing end of the needle, said flashback chamber having an opening at its trailing end;
an air bleeder plug removably secured to the trailing end of the flashback chamber, the plug comprising means substantially closing the trailing end opening of the flashback chamber, said closing means comprising sidewall means and narrow slit means disposed in said sidewall means accommodating passage of air while substantially preventing passage of blood through the slit means;
said plug comprising a hollow cylindrical shell and said closing means comprises a partition spanning across the hollow interior of the shell, said partition comprising an axial interiorly hollow projection having a blunt leading end and a truncated conical sidewall in which a plurality of slits are longitudinally disposed, said partition further comprising an annular ring integrally interposed between the trailing portion of the projection and the shell, the hollow interior of the projection being triangular in shape and the apexes of said triangle comprise said slits.

7. An intravenous needle assembly comprising:
a hollow pointed needle;
a hub secured to the proximal end of said needle, said hub being integral with a transparent blood detecting chamber;
an air bleed plug removably secured into said chamber, said plug having an axial opening therethrough with an interior annular shoulder disposed towards one end of said plug, said shoulder supporting a projection which extends outwardly past the end of said plug, said projection having a hollow interior cavity and said projection carrying a plurality of sidewall continuously open elongated narrow slits permitting the passage of egress air from said chamber to the exterior of said plug under force of the blood entering the chamber after venipuncture while substantially preventing the passage in the same direction of egress blood through said plug, the elongation of each said continuously open slit embodying a substantial longitudinal dimension.

8. The intravenous needle assembly of claim 7 wherein the exterior of said projection is a truncated cone.

9. The intravenous needle assembly of claim 7 further comprising a flexible plastic intravenous catheter disposed over said needle, said catheter is secured to a firm plastic needle hub sheath which is removably secured to the end of said needle hub.

10. A catheter placement assembly comprising:
a needle for penetrating the vein of a patient;
a catheter tube to be placed in the vein and left indwelling after venipuncture;
a flashback chamber connected to the trailing end of the needle, said flashback chamber having an opening at its trailing end;
an air bleeder plug removably secured to the trailing end of the flashback chamber, the plug comprising means substantially closing the trailing end opening of the flashback chamber, said closing means comprising sidewall means and narrow slit means disposed in said sidewall means accommodating passage of air while substantially preventing passage of blood through the slit means, the interior of said projection comprising an equilateral triangular cavity, the apexes of said triangular cavity being the slits carried by said projection.

* * * * *